US009923558B2

United States Patent
Southern et al.

(10) Patent No.: US 9,923,558 B2
(45) Date of Patent: Mar. 20, 2018

(54) VOLTAGE SOURCE DRIVER FOR A PARALLEL RESONANT MAGNETIC FIELD GENERATOR

(71) Applicant: Resonant Circuits Ltd, London (GB)

(72) Inventors: Paul Southern, Hertfordshire (GB); Simon Hattersley, Bickley (GB)

(73) Assignee: RESONANT CIRCUITS LIMITED, London (GB)

( * ) Notice: Subject to any disclaimer, the term of this patent is extended or adjusted under 35 U.S.C. 154(b) by 0 days.

(21) Appl. No.: 14/726,903

(22) Filed: Jun. 1, 2015

(65) Prior Publication Data

US 2016/0352329 A1 Dec. 1, 2016

(51) Int. Cl.
*H03K 3/00* (2006.01)
*H03K 17/687* (2006.01)
(Continued)

(52) U.S. Cl.
CPC ............. *H03K 17/687* (2013.01); *A61N 2/02* (2013.01); *H02J 50/10* (2016.02); *H03K 5/13* (2013.01);
(Continued)

(58) Field of Classification Search
CPC ................. H03K 17/687; H03K 5/13; H03K 2005/00019; H05B 6/10; H05B 6/40; A61N 2/02
(Continued)

(56) References Cited

U.S. PATENT DOCUMENTS 5,200,672 A * 4/1993 Sheynberg ......... H05B 41/2806
  315/248
5,233,577 A * 8/1993 Bakx ................. G11B 11/10508
  360/59
(Continued)

FOREIGN PATENT DOCUMENTS

| EP | 2407564 A1 | 1/2012 |
|---|---|---|
| GB | 2505278 A | 2/2014 |
| WO | 2014033773 A1 | 3/2014 |

OTHER PUBLICATIONS

Li Jingang, et al. "Study on a New Way of Load-matched for Voltage-Source Induction Heating Inverters" School of Automation and Information Engineering, ICIEA [2006].
(Continued)

*Primary Examiner* — Kenneth B Wells
(74) *Attorney, Agent, or Firm* — K&L Gates LLP

(57) ABSTRACT

A magnetic field generator. In one embodiment, the magnetic field generator includes a drive circuit including a MOSFET gate driver having an output terminal; a drive capacitor having a first and second terminal, a tank circuit including a tank circuit capacitor having a first and second terminal and a field-producing coil having a first and second terminal, wherein the first terminal of the tank circuit capacitor and the first terminal of the field-producing coil comprise the first terminal of the tank circuit, wherein the second terminal of the tank circuit capacitor and the second terminal of the field-producing coil comprise the second terminal of the tank circuit, wherein the first terminal of the drive capacitor is in electrical communication with the output terminal of the MOSFET gate driver, and wherein the second terminal of the drive capacitor is in electrical communication with the first terminal of the tank circuit.

13 Claims, 3 Drawing Sheets

(51) Int. Cl.
*A61N 2/02* (2006.01)
*H03K 5/13* (2014.01)
*H05B 6/10* (2006.01)
*H05B 6/40* (2006.01)
*H02J 50/10* (2016.01)
*H05B 6/06* (2006.01)
*H05B 6/42* (2006.01)
*H03K 5/00* (2006.01)

(52) U.S. Cl.
CPC ............... *H05B 6/06* (2013.01); *H05B 6/062* (2013.01); *H05B 6/10* (2013.01); *H05B 6/40* (2013.01); *H05B 6/42* (2013.01); *H03K 2005/00019* (2013.01)

(58) Field of Classification Search
USPC .................................................. 600/9, 13, 14
See application file for complete search history.

(56) References Cited

U.S. PATENT DOCUMENTS 7,348,847 B2 * 3/2008 Whittaker ............. H03F 1/0211
 330/250
2002/0125244 A1 9/2002 Yokozeki et al.

OTHER PUBLICATIONS

Search Report from related European patent application No. EP16171731 dated Oct. 4, 2016.

* cited by examiner

VOLTAGE SOURCE DRIVER FOR A PARALLEL RESONANT MAGNETIC FIELD GENERATOR

FIELD OF THE INVENTION

The invention relates generally to magnetic field generators for use in magnetic induction heating or hyperthermia treatment and more specifically to drivers for such generators.

BACKGROUND OF THE INVENTION

Magnetic field generators are used to generate alternating magnetic fields for domestic or industrial induction heating uses or hyperthermia treatments. An alternating magnetic field is produced by passing an alternating current through a coil. Generators of large alternating magnetic fields employ the resonant principle, in which energy passes back and forth at the characteristic resonant frequency between the magnetic field associated with current in a coil and the electric field associated with voltage across a capacitor. The advantage of this technique is that the power source need only compensate for losses, rather than supplying the full magnetic field energy on every cycle. There are two standard circuit configurations used in this technique: series resonant and parallel resonant.

In a series resonant system, the coil is made to operate at the intended frequency by a capacitor placed in series with it. In this configuration, the entire current through the coil also flows in the power source, which becomes a limiting factor. To obtain a large field (in volume and/or intensity) using a moderate current flow requires a coil of many turns, which has high inductance. The effect of the series resonance is then to create an extremely high voltage across the coil, possibly reaching tens of kilovolts, which is a problem for insulation and capacitor rating, and can even result in corona discharge in the air. The series resonant configuration is readily driven by a simple voltage source. However, because of engineering and safety considerations related to high voltage and the impracticality of operation at high frequencies (for example, above 100 kHz), series resonance is not preferred for generating large high-frequency magnetic fields.

In a parallel resonant system, the coil is made to operate at the intended frequency by a capacitor placed in parallel with it. In this configuration, the resonance amplifies the current flowing in the coil to far higher levels than the capability of the power source. A large field can be created with a coil of few turns and relatively low inductance such that the voltage is much lower than for series resonance, and higher frequency operation becomes practicable. This is the preferred configuration for generating large, high-frequency magnetic fields, but has the drawback that conventionally inductive components (matching inductors or high-frequency transformers) are used in providing an effective current source to drive it. These components add to complexity and power loss, and may also result in damaging voltage spikes if the power source becomes de-tuned from the resonance.

What is required is an efficient, scalable driver that is able to produce a high magnetic field at high frequency in a low inductance coil.

The present invention addresses this need.

SUMMARY OF THE INVENTION

The invention relates to a magnetic field generator. In one embodiment, the magnetic field generator includes a drive circuit including a MOSFET gate driver having an output terminal, a drive capacitor having a first terminal and a second terminal, a tank circuit including a tank circuit capacitor having a first terminal and a second terminal and a field-producing coil having a first terminal and a second terminal, wherein the first terminal of the tank circuit capacitor and the first terminal of the field-producing coil comprise the first terminal of the tank circuit and wherein the second terminal of the tank circuit capacitor and the second terminal of the field-producing coil comprise the second terminal of the tank circuit, wherein the first terminal of the drive capacitor is in electrical communication with the output terminal of the MOSFET gate driver, and wherein the second terminal of the drive capacitor is in electrical communication with the first terminal of the tank circuit. In one embodiment, the second terminal of the tank circuit is connected to the power supply ground.

In another embodiment, the drive circuit includes a plurality of MOSFET gate drivers and a plurality of drive capacitors, wherein each respective MOSFET gate driver is in electrical communication with the first terminal of a respective drive capacitor, and wherein the second terminal of each respective drive capacitor is in electrical communication with the first terminal of the tank circuit.

In another embodiment, the drive circuit further includes a sense coil positioned so as to sense the rate of change of current in the magnetic field coil; a coil integrator circuit having an input terminal connected to the sense coil and having an output terminal; a delay compensation circuit having an input terminal connected to the output terminal of the coil integrator circuit and having an output terminal; and a comparator having an input terminal connected to the output terminal of the delay compensation circuit and having an output terminal, wherein the MOSFET gate driver has an input terminal connected to the output terminal of the comparator. In one embodiment, the sense coil is a Rogowski coil and the coil integrator is a Rogowski coil integrator.

In one embodiment, the drive capacitor comprises a capacitor array, wherein the capacitor array includes one or more capacitor chains, wherein each capacitor chain includes one or more capacitors connected in series, and wherein each capacitor chain is connected in parallel to the other capacitor chains of the array. In another embodiment, the capacitor array is a single capacitor. In another embodiment, the second terminal of the tank circuit is connected to a common power supply ground through a second drive capacitor array. In yet another embodiment, the field-producing coil includes Litz wire running along an outer surface of a copper pipe.

BRIEF DESCRIPTION OF THE DRAWINGS

The structure and function of the invention can be best understood from the description herein in conjunction with the accompanying figures. The figures are not necessarily to scale, emphasis instead generally being placed upon illustrative principles. The figures are to be considered illustrative in all aspects and are not intended to limit the invention, the scope of which is defined only by the claims.

DESCRIPTION OF A PREFERRED EMBODIMENT

Figure 1:
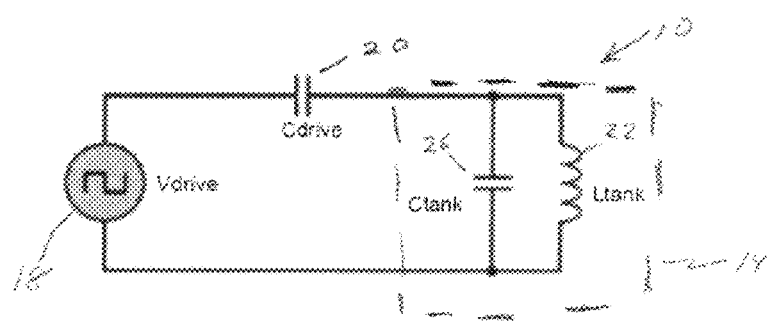
FIG. 1 is an idealized schematic diagram of an embodiment of a magnetic field generator constructed in accordance with the invention.

In brief overview and referring to FIG. 1, a magnetic generator 10 constructed in accordance with the invention generates a sinusoidal magnetic field by driving a tank circuit 14 using a square-wave voltage source 18 through a drive capacitance 20. The tank circuit 14 includes a field-producing coil 22 and a parallel reservoir capacitance 26. The square wave voltage source 18 is constructed to drive the tank circuit 14 at its natural resonance.

Previous commentators have declared that the configuration of FIG. 1 is not functional due to the large current spikes that occur on the switching devices caused by the capacitor 20 in series with the tank circuit 14. For example, the paper *Study on a New Way of Load-matched for Voltage-Source Induction Heating Inverters*, L. Jingang et al., ICIEA 2006, states: "The voltage source induction heating supply generally required the condition of R>r. The LCL type topology of FIG. 2(c) cannot satisfy this demand. It is obviously for the inverter that the FIG. 2(b) [FIG. 1 of this patent application.] LCC topology exists two series capacitances load, which will generate current impulse on switch devices. Especially existing instantaneous short circuit, it's unallowed in voltage inverter." The authors then describe another LCL configuration as a preferred configuration. The present invention uses MOSFET devices that are designed to drive a capacitive load, operating at reduced switching speeds to prevent large spikes, thus avoiding damage to the devices.

To understand the operation of the circuit, consider the idealized circuit of FIG. 1 when circuit losses are included. In the idealized circuit of FIG. 1, when losses are neglected, the alternating current in the tank circuit 14 will rise indefinitely as energy is pumped into the tank circuit by the square wave voltage source 18. If one accounts for current-related losses in each branch of the circuit, the circuit shown in FIG. 2A results, where $R_x$ 30, $R_C$ 34, and $R_L$ 38 are the resistive losses associated with the drive capacitance $C_X$ 20, the reservoir capacitance of the tank circuit $C_T$ 26, and the tank circuit coil $L_T$ 22, respectively.

Figure 2A:
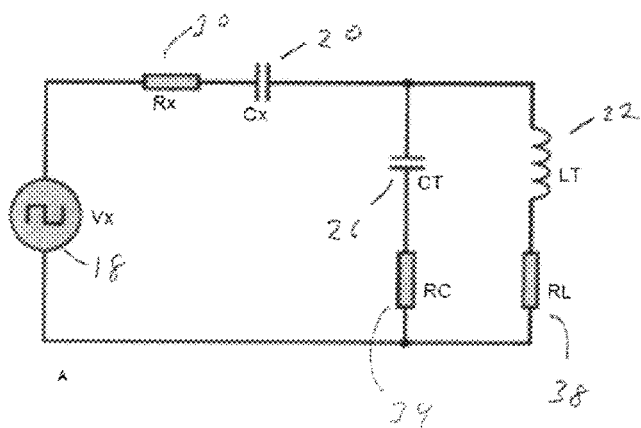
FIG. 2A is a schematic diagram of the embodiment of a magnetic field generator of FIG. 1 including resistive losses.
Figure 2B:
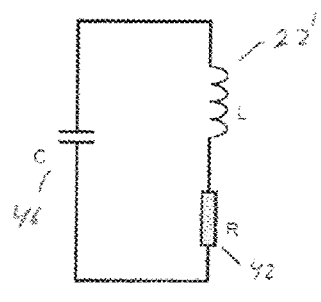
FIG. 2B is the equivalent circuit of FIG. 2A.

To calculate the total power loss and resonant frequency of this circuit, the circuit of FIG. 2A is simplified to an equivalent circuit shown in FIG. 2B. This is accomplished by incorporating any resistance of the voltage drive into series resistance $R_X$, and treating the voltage source $\pm V_X$ as having zero resistance. The inductance $L_T$ is the same as L in the equivalent circuit, C is the parallel combination of $C_X$ and $C_T$ (as viewed from the coil) in the equivalent circuit and R is a combination of $R_X$, $R_C$ and $R_L$. Using the FIG. 2B terminology, and assuming low damping (high Q factor), it is readily shown that:

$$L = L_T$$
$$C = C_T + C_X$$

$$R = R_L + \frac{R_X}{\left(1 + \frac{C_T}{C_X}\right)^2} + \frac{R_C}{\left(1 + \frac{C_X}{C_T}\right)^2}$$

The operating frequency is close to the natural frequency for the equivalent capacitance and inductance:

$$\omega = \frac{1}{\sqrt{LC}}$$

where $\omega$ is the angular frequency, $\omega = 2\pi f$

An AC steady-state condition occurs when the system has run for a sufficient time such that the peak amplitude of the current and voltage waveforms ($I_p$ and $V_p$) at the field coil 22 are constant. At this point, the conservation of energy requires that the electrical power delivered from the drive circuit 18 equals the thermal power lost to the environment. All the currents are close to sinusoidal, despite the fact that the drive circuit is a square-wave voltage drive, because of the high-Q of the resonant system.

The relation between peak voltage $V_P$ and current $I_P$ at the field coil 22' is:

$$I_P = V_P \omega C = \frac{V_P}{\omega L}$$

The power loss is determined from the peak current and the equivalent resistance:

$$P_{loss} = \frac{I_P^2 R}{2}$$

The power delivered to the tank circuit 14 is determined by integrating the product of the drive voltage (square-wave) and the drive current (sine-wave resulting from the large tank voltage applied across the drive capacitance) over half a cycle:

$$I_X = V_P \omega C_X = I_P \frac{C_X}{C} \quad \text{peak drive current}$$

$$P_{in} = \frac{\omega}{\pi} \int_0^{\frac{\pi}{\omega}} V_X I_X \sin\omega t \, dt = \frac{\omega}{\pi} V_X I_X \left[\frac{-\cos\omega t}{\omega}\right]_0^{\frac{\pi}{\omega}} = \frac{2}{\pi} V_X I_X$$

$$\Rightarrow P_{in} = \frac{2}{\pi} V_X I_P \frac{C_X}{C}$$

In practice, rather than using a voltage which switches symmetrically between a negative and a positive voltage, it is more convenient to use a single power supply $V_S$ and switch between 0 and $V_S$. The DC offset does not matter because of the capacitive coupling.

substitute $V_S = 2V_X$ $$\Rightarrow P_{in} = \frac{1}{\pi} V_S I_P \frac{C_X}{C}$$

require $P_{loss} = P_{in}$ $$\Rightarrow \frac{I_P^2 R}{2} = \frac{1}{\pi} V_S I_P \frac{C_X}{C}$$

$$\Rightarrow I_P = \frac{2}{\pi} V_S \frac{C_X}{CR}$$

The peak current in the field coil is independent of the inductance, but a change of inductance will alter the frequency of the tank circuit 14. In one embodiment, the tank capacitor 26 is much larger than the drive capacitance 20 so as to allow very high currents to be developed in a low inductance coil 22. A circuit constructed according to the invention can operate with any ratio between drive capacitance 20 and tank capacitance 26, progressively moving from parallel resonance towards series resonance as the drive capacitance 20 is increased relative to the tank capacitance 26. A larger value of drive capacitance 20 can be useful to increase the current in the coil 22 without using a higher power supply voltage, especially where multiple drive channels are used to share the drive current. In one embodiment, the coil is constructed of Litz wire, discussed below, which helps maintain a high Q-factor by reducing resistive losses. In the embodiment discussed herein, the circuit uses MOSFET gate drivers which are capacitively coupled to the tank circuit 14 in a hybrid configuration topology.

Figure 3:
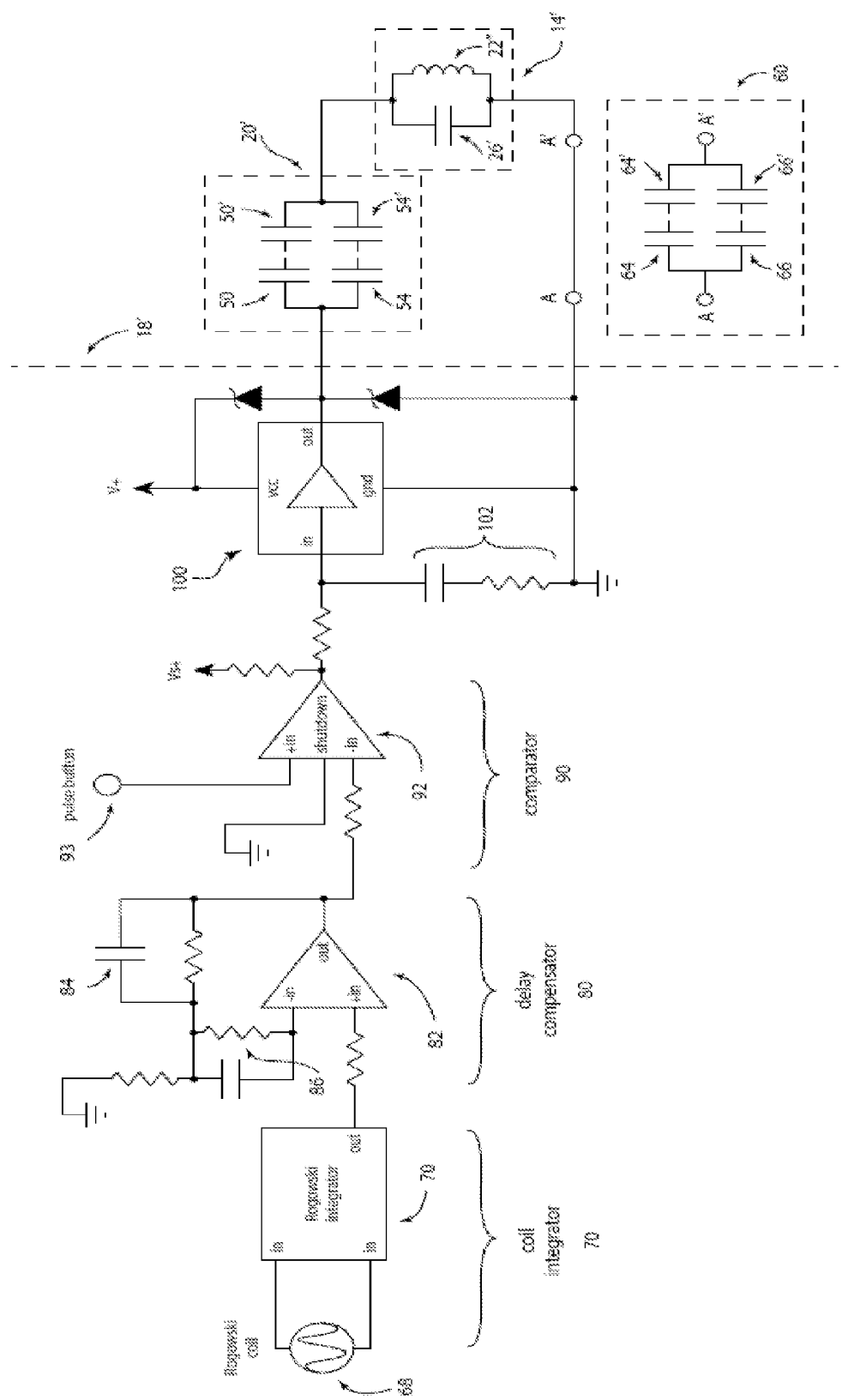
FIG. 3 is a schematic diagram of an embodiment of the magnetic field generator of the invention.

Referring to FIG. 3, one embodiment of the circuit includes a voltage circuit 18', a drive capacitor array 20' and a tank circuit 14'. Considering each component separately, the drive capacitor array 20', in one embodiment, includes two pairs of series-connected capacitors 50, 50' and 54, 54', each pair connected together in parallel with the other. One terminal of the drive capacitor array is connected to the drive circuit 18' and the other terminal of the drive capacitor array 20' is connected to one terminal of the tank circuit 14', discussed below. The reason for this is to double both the voltage rating and the current rating relative to using a single capacitor of the same value. Further, in one embodiment a second drive capacitor array 60 that includes two pairs of series-connected capacitors 64, 64" and 66, 66', each pair connected together in parallel with the other, is connected to a second terminal of the tank circuit 14' (at AA' in the diagram) to provide a symmetric return path. In other embodiments, additional drive channels are connected in parallel to supply the power requirements of the generator.

Figure 4:
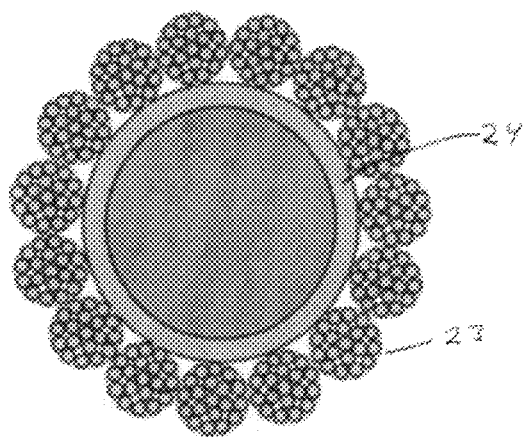
FIG. 4 is a cross-sectional diagram of an embodiment of the field-producing coil of the tank circuit of the invention as constructed with Litz wire wound along a pipe.
Figure 5:
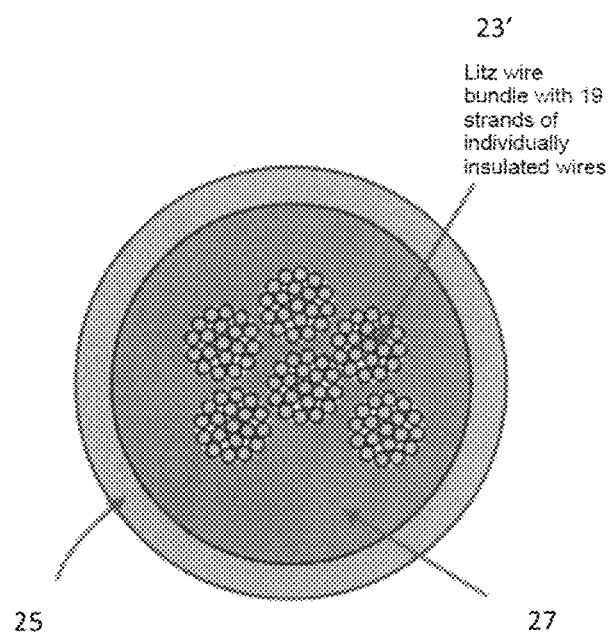
FIG. 5 is a cross-sectional diagram of an embodiment of the field-producing coil of the tank circuit of the invention as constructed with Litz wire positioned internal to a pipe.

The tank circuit 14' includes a capacitor 26' connected in parallel with a magnetic-field producing coil 22". In one embodiment, the magnetic field-producing coil 22" is constructed of Litz wire 23 wound along a copper pipe 24 (FIG. 4), to form a coil. A cooling fluid passes through the pipe. The benefit of using Litz wire, where the conductor is divided into many fine, insulated strands woven in a special pattern, is that it minimizes both skin effect and proximity effect. In conventional bulk conductors, these effects constrain high frequency current to flow in limited regions of the cross-section of the conductors, drastically increasing the resistance. FIG. 5 is yet another embodiment of a magnetic field-producing coil constructed of Litz wire 23 running within a non-conductive pipe 25, such as plastic, which forms a coil and through which is passed a non-conducting cooling fluid 27, such as distilled water or oil.

In one embodiment, the drive circuit 18' includes a sense coil 68, a coil integrator circuit 70, an optional delay compensation circuit 80, a comparator circuit 90, and a MOSFET gate driver circuit 100. Considering each separately, the sense coil is positioned to monitor the current flow through the field coil 22'. In one embodiment, the sense coil is a Rogowski coil. In one embodiment, the sense coil 68 is wrapped about one terminal of the field coil 22" or the wires going to that terminal. In one embodiment, the voltage induced in the sense coil 68, which is proportional to the rate of change of current in the monitored conductor, is an input signal to the coil integrator circuit 70.

The output of the sense coil integrator 70 representing the current in the field coil 22' is connected to the positive input of an ADA4899 high speed operational amplifier 82 (Analog Devices Incorporated, Norwood, Mass., USA 02062) used as the delay compensation circuit 80. The output terminal of the high speed operational amplifier 82 is connected to the negative input of a second ADA4899 operational amplifier 92 through a resistor capacitor network 84 that includes a variable resistor 86. The variable resistor 86 is used to set a frequency-dependent phase advance that is equivalent to a negative delay. This compensates for the switching time of the MOSFET gate driver 100, improving performance. The output signal of the delay compensation circuit 80 is an input signal to the high speed linear comparator circuit 90. In another embodiment, the delay compensation circuit 80 is not used, and the output of the integrator 70 is the input of the comparator circuit 90.

In one embodiment, the high speed linear comparator circuit 90 includes a high speed comparator 92 LT1719 (Linear Technology Corporation, Milpitas, Calif., USA, 95035-7417). The output signal of the delay compensation circuit 80 is connected to the negative input terminal of the high speed comparator 92. The positive input 93 of the comparator is normally at ground potential, but it can be pulsed to a higher potential by a push-button to initiate the coil resonance. The resulting comparison of the signal value from the delay compensation circuit 80 and ground potential of zero volts is the output signal of the comparator 90 generating the square wave.

The output of the comparator 90, in one embodiment, is the input signal to a MOSFET gate driver 100 IXD630 (IXYS Integrated Circuits Division, Beverly, Mass. USA 01915-1048). This device operates from a power supply voltage $V_S$ in the range 12.5 V to 35 V. High voltages only occur on the far side of the drive capacitor 20' which is connected to the tank circuit 14'. Power is supplied to the MOSFET gate driver 100 via a capacitor bank positioned close to the device to minimize power rail disturbances when the device switches. Zener diodes between the output terminal and the power rails protect the driver 100 if the power supply to the circuit is removed while the resonant circuit is still oscillating.

In operation, the current measured by the sense coil 68 and its associated coil integrator 70 is advanced by a set amount by the delay compensation circuit 80. The output of the delay compensation circuit 80 is then compared to zero volts with a high speed comparator 90. Thus, whenever the current measured by the sense coil subsystem recrosses zero, the output of the comparator 90 will switch, generating a square wave. The output of the comparator 90 is the input to a MOSFET gate driver 100. The output of the MOSFET gate driver 100 drives the capacitor array 20'. A second terminal of the capacitor array 20' is connected to the tank circuit 14'.

Although the circuit is shown and described as having a MOSFET gate driver, in another embodiment the drive circuit includes a plurality of MOSFET gate drivers and a plurality of drive capacitors. In this embodiment, each respective MOSFET gate driver 100 is in electrical communication with the first terminal of a respective drive capacitor 20'. The second terminal of each respective drive capacitor is in electrical communication with the first terminal of the tank circuit. The ability to add more drive channels in parallel allows the circuit to scale up to higher field levels as needed.

This configuration of the magnetic field generator permits the gate driver 100 to tolerate any resulting current or voltage spikes caused by the switching of the tank circuit 14'.

Unless otherwise indicated, all numbers expressing lengths, widths, depths, or other dimensions, and so forth used in the specification and claims are to be understood in all instances as indicating both the exact values as shown and as being modified by the term "about" or "substantially". Accordingly, unless indicated to the contrary, the numerical parameters set forth in the specification and attached claims are approximations that may vary depending upon the desired properties sought to be obtained. Variations of various parameters of ±10% are contemplated.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

It should be understood that the order of steps or order for performing certain actions is immaterial so long as the present teachings remain operable. Moreover, two or more steps or actions may be conducted simultaneously.

The terms "a," "an," "the," and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Variations on the described embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A magnetic field generator comprising:
   a drive circuit comprising:
      at least one MOSFET gate driver device having an output terminal,
      a sense coil positioned so as to sense the rate of change of current in a magnetic field-producing coil;
      a coil integrator circuit having an input terminal connected to the sense coil and having an output terminal; and
      a comparator having an input terminal connected to the output terminal of the coil integrator circuit and having an output terminal,
      wherein the at least one MOSFET gate driver device has an input terminal in electrical communication with the output terminal of the comparator;
   a tank circuit comprising:
      a first terminal and a second terminal;
      a tank circuit capacitor having a first terminal and a second terminal;
      the magnetic field-producing coil having a first terminal and a second terminal;
      wherein the first terminal of the tank circuit capacitor and the first terminal of the magnetic field-producing coil comprise the first terminal of the tank circuit,
      wherein the second terminal of the tank circuit capacitor and the second terminal of the magnetic field-producing coil comprise the second terminal of the tank circuit; and
   at least one drive capacitor having a first terminal and a second terminal,
      wherein the first terminal of the at least one drive capacitor is in electrical communication with the output terminal of the at least one MOSFET gate driver device,
      wherein the second terminal of the at least one drive capacitor is in electrical communication with the first terminal of the tank circuit, and
      wherein there is at least one drive capacitor in electrical communication with each of the at least one MOSFET gate driver device.

2. The magnetic field generator of claim 1, further comprising a delay compensation circuit connected between the coil integrator circuit and the comparator circuit, the delay compensation circuit having an input terminal connected to the output terminal of the coil integrator circuit and having an output terminal connected to the input terminal of the comparator circuit.

3. The magnetic field generator of claim 1, wherein the at least one drive capacitor comprises a plurality of drive capacitors, each of the plurality of drive capacitors comprising an input terminal and an output terminal, and wherein the drive circuit includes a plurality of MOSFET gate driver devices, each of the plurality of MOSFET gate driver devices comprising an input terminal and an output terminal, a respective output terminal of each of the plurality of MOSFET gate driver devices being in electrical communication with the input terminal of a respective one of the plurality of drive capacitors, wherein the output terminal of each of the plurality of drive capacitors is in electrical communication with the first terminal of the tank circuit.

4. The magnetic field generator of claim 1, wherein the second terminal of the tank circuit is connected to a power supply ground.

5. The magnetic field generator of claim 1,
wherein the at least one drive capacitor comprises at least one capacitor array,
wherein the at least one capacitor array comprises one or more capacitor chains,
wherein each capacitor chain comprises one or more capacitors connected in series, and wherein each capacitor chain is connected in parallel with the other capacitor chains of the first capacitor array.

6. The magnetic field generator of claim 1, wherein the sense coil is a Rogowski coil.

7. The magnetic field generator of claim 5, wherein the second terminal of the tank circuit is connected to a power supply ground through a second drive capacitor array.

8. The magnetic field generator of claim 1, wherein the magnetic field-producing coil comprises Litz wire wound along a copper pipe configured to permit a cooling fluid to pass through the copper pipe.

9. The magnetic field generator of claim 1, wherein the magnetic field-producing coil comprises Litz wire within a non-conductive pipe to form a coil and configured to permit a nonconductive cooling fluid to pass through the non-conductive pipe.

10. The magnetic field generator of claim 2 wherein the delay compensation circuit includes a variable resistor to adjust the switching time of the at least one MOSFET gate driver device.

11. A method of generating a magnetic field in a circuit comprising: a tank circuit comprising a field generating coil, the tank circuit connected in series with a first terminal of at least one drive capacitor, a second terminal of the at least one drive capacitor being connected to an output terminal of at least one MOSFET gate driver, the method comprising the steps of:
providing a square-wave voltage to the drive capacitor array using the at least one MOSFET gate driver;
providing charge pulses to the tank circuit from the drive capacitor array to drive the tank circuit resonance and thereby cause the field generating coil to generate a magnetic field; and
switching the at least one MOSFET gate driver in response to a comparison of a signal responsive to the generated magnetic field with a reference voltage that is substantially 0.

12. The method of claim 11 wherein the reference voltage is pulsed away from 0 to start the oscillation.

13. The method of claim 11, further comprising the step of generating a delay-compensated signal by applying an adjustable phase advance to an integrated signal from a sense coil.

* * * * *